(12) United States Patent
Wu et al.

(10) Patent No.: US 11,638,520 B2
(45) Date of Patent: May 2, 2023

(54) OPHTHALMIC IMAGING SYSTEM

(71) Applicant: SVISION IMAGING LIMITED, Henan (CN)

(72) Inventors: Heng Wu, Henan (CN); Xianzhao Peng, Henan (CN); Nanfan Cheng, Henan (CN)

(73) Assignee: SVISION IMAGING LIMITED, Henan (CN)

( * ) Notice: Subject to any disclaimer, the term of this patent is extended or adjusted under 35 U.S.C. 154(b) by 361 days.

(21) Appl. No.: 16/853,743

(22) Filed: Apr. 20, 2020

(65) Prior Publication Data

US 2020/0245864 A1 Aug. 6, 2020

Related U.S. Application Data

(63) Continuation-in-part of application No. PCT/CN2018/110791, filed on Oct. 18, 2018.

(30) Foreign Application Priority Data

Oct. 20, 2017 (CN) .......................... 201710991897.2
Jul. 18, 2018 (CN) .......................... 201810799715.6
Jul. 18, 2018 (CN) .......................... 201821150335.1

(51) Int. Cl.
*G01B 9/02* (2022.01)
*A61B 3/10* (2006.01)
(Continued)

(52) U.S. Cl.
CPC ............ *A61B 3/102* (2013.01); *A61B 3/1225* (2013.01); *G01B 9/02091* (2013.01)

(58) Field of Classification Search
CPC ......... A61B 3/102; A61B 3/1225; A61B 3/14; G01B 9/02091; G01B 9/02029; G01B 9/0203

See application file for complete search history.

(56) References Cited

U.S. PATENT DOCUMENTS 8,427,654 B2 * 4/2013 Horn .................. G01B 9/02077
356/497
2007/0291277 A1 * 12/2007 Everett .............. G01B 9/02077
356/497

(Continued)

*Primary Examiner* — Tarifur R Chowdhury
*Assistant Examiner* — Jonathon Cook
(74) *Attorney, Agent, or Firm* — JCIP Global Inc.

(57) ABSTRACT

An ophthalmic imaging system including an ocular lens and an optical coherence tomography (OCT) imaging module is provided. The OCT imaging module is able to image both retina and anterior segment of eyes by switching a lens group into and out of the OCT light path. The OCT imaging module includes a retina imaging mode and an anterior segment imaging mode. In the retina imaging mode, there exists an intermediate image plane located between the ocular lens and the OCT imaging module. From the retina imaging mode, anterior segment imaging is achieved by inserting a switching lens group into the optical path inside the OCT imaging module or replacing the whole OCT imaging module of the retina mode, wherein, after the insertion, there exist a new intermediate image plane located inside the OCT imaging module and a conjugate of the entrance pupil of the OCT imaging module located between the ocular lens and the OCT imaging module.

16 Claims, 13 Drawing Sheets

(51) Int. Cl.
*A61B 3/12* (2006.01)
*G01B 9/02091* (2022.01)

(56) References Cited

U.S. PATENT DOCUMENTS

| | | | | |
|---|---|---|---|---|
| 2008/0106696 A1* | 5/2008 | Buckland | ............... | A61B 3/102 |
| | | | | 351/206 |
| 2011/0102802 A1* | 5/2011 | Izatt | ................... | G01B 9/0201 |
| | | | | 356/479 |
| 2012/0140238 A1* | 6/2012 | Horn | ................. | G01B 9/02077 |
| | | | | 356/479 |
| 2014/0198300 A1* | 7/2014 | Goto | ................ | G01B 9/02044 |
| | | | | 351/246 |
| 2016/0166147 A1* | 6/2016 | Peschka | ............... | A61B 3/1225 |
| | | | | 351/221 |
| 2019/0076012 A1* | 3/2019 | Kobayashi | ............ | A61B 3/107 |

* cited by examiner

OPHTHALMIC IMAGING SYSTEM

CROSS-REFERENCE TO RELATED APPLICATION

This application is a continuation in part of international PCT application serial no. PCT/CN2018/110791, filed on Oct. 18, 2018, which claims the priority benefit of China application no. 201710991897.2, filed on Oct. 20, 2017, China application no. 201810799715.6, filed on Jul. 18, 2018 and China application no. 201821150335.1, filed on Jul. 18, 2018. The entirety of each of the above-mentioned patent applications is hereby incorporated by reference herein and made a part of this specification.

BACKGROUND

Technical Field

The present invention relates to an ophthalmic imaging system.

Description of Related Art

Optical coherence tomography (OCT) technology has the characteristics of high resolution, high imaging speed and non-invasion. Ophthalmic imaging is one of the most popular applications of the OCT technology.

Please refer to FIG. 1, U.S. Pat. No. 8,427,654 introduces an optical design of an ophthalmic imaging apparatus including an OCT path, especially a switching method of retina and anterior segment imaging optical paths. By introducing a lens group into the OCT optical path, the focal plane position of the ocular lens group moves from the retina to the anterior segment. The advantage of that method is that the structure is relatively simple, but the field of view of the anterior segment is small and it is inflexible to control the angle of the light incident on the target.

Please refer to FIG. 2, Patent US20080106696A1 introduces an OCT system for the measurement of the refractive index of eyes, especially including both retina and anterior segment imaging modes. Similar to U.S. Pat. No. 8,427,654, the focal plane position of the ocular lens attachment is moved from the posterior segment of the eye to the anterior segment by inserting a lens group into the OCT optical path.

Please refer to FIGS. 3, 4 and 5, Patent CN102438505ZHONG introduces an OCT system which also includes a switching method between anterior segment and posterior segment. By adding a dichroic mirror and a rotating the reflector close to the scanning mirror by 90 degrees, the anterior segment optical path is replaced by the posterior segment optical path and connected to the subsequent optical path. The dashed box 1a1 is the retina imaging mode and the dashed box 1b1 the anterior segment imaging mode.

Please refer to FIG. 6, Patent US2008/0106696A1 introduces an OCT system. In the retina imaging mode, another ocular lens is added as an attachment at the original eye position so as to move the imaging conjugate from the retina to the anterior segment. However, this method has the problem that the imaging quality of the fixation optical path is compromised. For the eye to be tested, the fixation target will become blurred after switching to the anterior segment.

In the current ophthalmic OCT market, a considerable number of products cover both imaging functions of anterior and posterior segments. There are different ways to switch between those two imaging modes.

External switching methods, such as Patent US2008/0106696A1, require manual operation of users, which is inconvenient to operate and difficult to maintain proper functions of the internal fixation target in both modes. Some internal switching methods, such as Patent CN102438505ZHONG, rely on multiple planar reflective optical elements to switch between two independent optical paths. According to other internal switching methods such as U.S. Pat. No. 8,427,654 and Patent US20080106696A1, switch imaging modes by moving the intermediate image plane inside the lens system to the front of the eye. In those approaches, the available field of view is limited. It can hardly support telecentric imaging and thus limits the capability of quantitative measurement.

Therefore, a new ophthalmic imaging system is needed to solve the aforementioned problems.

SUMMARY

In order to overcome the limitations in the prior art, an ophthalmic imaging system is provided.

According to an embodiment of the present invention, the ophthalmic imaging system includes an ocular lens and an optical coherence tomography (OCT) imaging module, wherein the OCT imaging module includes a retina imaging mode and an anterior segment imaging mode. In the aforesaid retina OCT imaging mode, the OCT imaging module contains a first intermediate image plane located between the ocular lens and the OCT imaging module. In order to image the anterior segment via the anterior segment imaging mode, a switching lens group is inserted into the aforesaid the OCT imaging module. A second intermediate image plane is formed inside the OCT imaging module. A conjugate of the entrance pupil of the OCT imaging module is added between the ocular lens and the OCT imaging module.

Further, in some embodiments, the ophthalmic imaging system includes a first dichroic mirror, wherein the OCT imaging module is arranged positioned on one side of the first dichroic mirror, the ocular lens is positioned on the reflective path of the first dichroic mirror. The first intermediate image plane is located between the ocular lens and the first dichroic mirror.

Further, in some embodiments, the optical path ratio of the retina imaging mode and the anterior segment imaging mode satisfies the following formula:

$$0.9 \leq \frac{OPL_{retina}}{OPL_{cornea}} \leq 1.1$$

where $OPL_{retina}$ represents the optical path length in the retina imaging mode measured from the entrance pupil of the OCT imaging module to the retina of a standard eye, and $OPL_{cornea}$ represents the optical path length in the anterior segment imaging mode, measured from the entrance pupil of the OCT imaging module to the iris of the standard eye. By following the aforesaid criteria, the optical design can ensure that optical lengths of sample arms remain approximately the same before and after switching between the retina imaging mode and the anterior segment imaging mode under the premise of considering the standard eye.

Further, in some embodiments, the ophthalmic imaging system includes a second dichroic mirror and a scanning laser ophthalmoscope (SLO) module, wherein the second dichroic mirror is positioned on the transmissive path or the reflective path of the first dichroic mirror, a first relay device is arranged on the light path between the second dichroic mirror and the first dichroic mirror, and the retina SLO module is arranged on the reflective path or the transmissive path of the second dichroic mirror.

Further, in some embodiments, the ophthalmic imaging system includes a third dichroic mirror, a fixation target module and a pupil camera module, wherein the third dichroic mirror is positioned on the transmissive path or the reflective path of the second dichroic mirror, a second relay device is positioned between the third dichroic mirror and the second dichroic mirror, the fixation target module is positioned on the transmissive path or the reflective path of the third dichroic mirror, and the anterior segment imaging module is positioned on the reflective path or the transmissive path of the third dichroic mirror.

Further, in some embodiments, the ophthalmic imaging system includes an OCT galvanometer, wherein the OCT galvanometer is positioned at the end, away from the first dichroic mirror, of the OCT imaging module. Further, the ophthalmic imaging system of the present invention includes a lens group switching device, which switches the switching lens group between the aforementioned two OCT imaging modes, namely the retina imaging mode and the anterior segment imaging mode.

Further, in some embodiments, the lens group switching device includes a base plate, a driving platform and a driving motor. The switching lens group is mounted in the base plate through a positioning block vertically mounted on the bottom plate. The driving platform is vertically fixed on the base plate. A ball screw connected with a rotating shaft of the driving motor is fixed on a horizontal part of the driving platform, a guide rail is fixed on a vertical part of the driving platform, and the vertical part of the driving platform is equipped with two photoelectric sensors in the longitudinal direction. The switching lens group assembly includes a lens group and a prepressing plate which is elastically connected with the lens group. A feed screw nut is connected with the ball screw, a slider capable of moving up and down along the guide rail is fixed on the prepressing plate, and a mechanical triggering part to trigger the two photoelectric sensors is also connected with the prepressing plate.

Further, in some embodiments, the ball screw is fixed in the based plate after passing through the feed screw nut and the prepressing plate.

Further, in some embodiments, the bottom of the switching lens group assembly is equipped with an annular positioning interface. A set of magnets are equidistantly mounted on the annular positioning area. There is a V-shaped groove between each pair of adjacent magnets, and the V-shaped grooves are also equidistantly positioned in the annular positioning interface. The base plate is also equipped with an annular positioning part, on which a set of magnets are equidistantly mounted. There is a steel ball between each pair of adjacent magnets, and the steel balls are equidistantly positioned in the annular positioning part. The magnets at the bottom of the lens group and the magnets on the base plate are positioned correspondingly. The steel balls are in kinetic contact with the V-shaped grooves when the lens group module is switched onto the base plate.

Further, in some embodiments, the bottom plate of the lens group is equipped with through holes. The prepressing plate is equipped with threaded holes matching the through holes. The switching lens group assembly and the prepressing plate are connected through connecting screws, which are sheathed in springs. The connecting screws sequentially pass through the springs and the through holes and are connected with the threaded holes by threads.

Based on the above, the embodiments of the present invention have the following beneficial effects: the disclosed ophthalmic imaging system is able to achieve OCT imaging of both anterior segment and retina by switching a lens group into or out of the optical path respectively. When the switching lens group is in the optical path and the system is in anterior segment imaging mode, a second intermediate image is formed in the optical path inside the switching lens group and a conjugate of the entrance pupil forms near the back focal plane of the ocular lens. The said design makes the imaging of the anterior segment telecentric or near telecentric. It also allows a more flexible control of the angle of the light entering the anterior segment and improves the achievable field of view and imaging resolution. Meanwhile, with the present invention, the switching of OCT imaging mode is contained within the OCT path and does not affect other optical paths of the system.

In addition, the switching between the two OCT imaging modes in the embodiments of the present invention is realized through the lens group switching device. The approach of the shared single optical path greatly reduces the space that the lens group switching device could have taken and the necessary number of optical and mechanical elements. The positioning module with kinetic contacts of steel balls and V-shaped grooves in the lens group switching device ensures high repeatability precision and greatly reduces difficulty of assembly and calibration. The lens group switching device is compact in structure, high in reliability and easy to assemble. It may also be configured to switch similar lens groups in a variety of other optical instruments and devices.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the invention.

DESCRIPTION OF THE EMBODIMENTS

Figure 1:
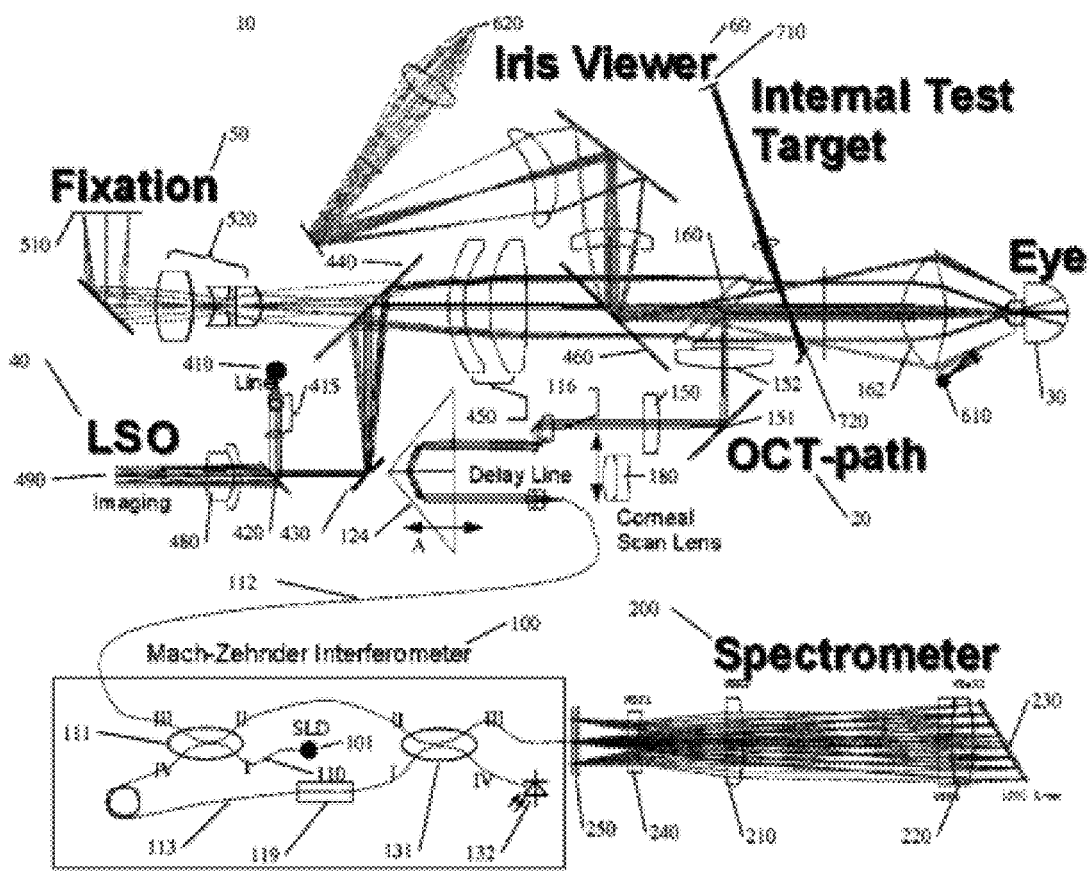
FIG. 1 is an optical path system diagram including the OCT path in U.S. Pat. No. 8427654.
Figure 2:
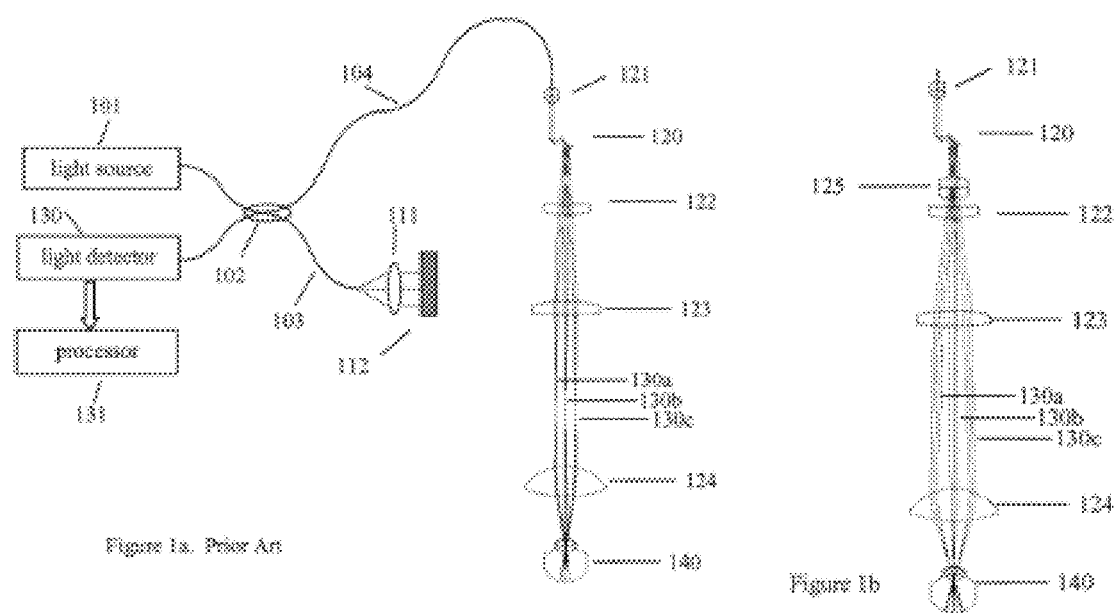
FIG. 2 is an optical path system diagram of the OCT system for the measurement of refractive index of eyes in patent US20080106696A1.
Figure 3:
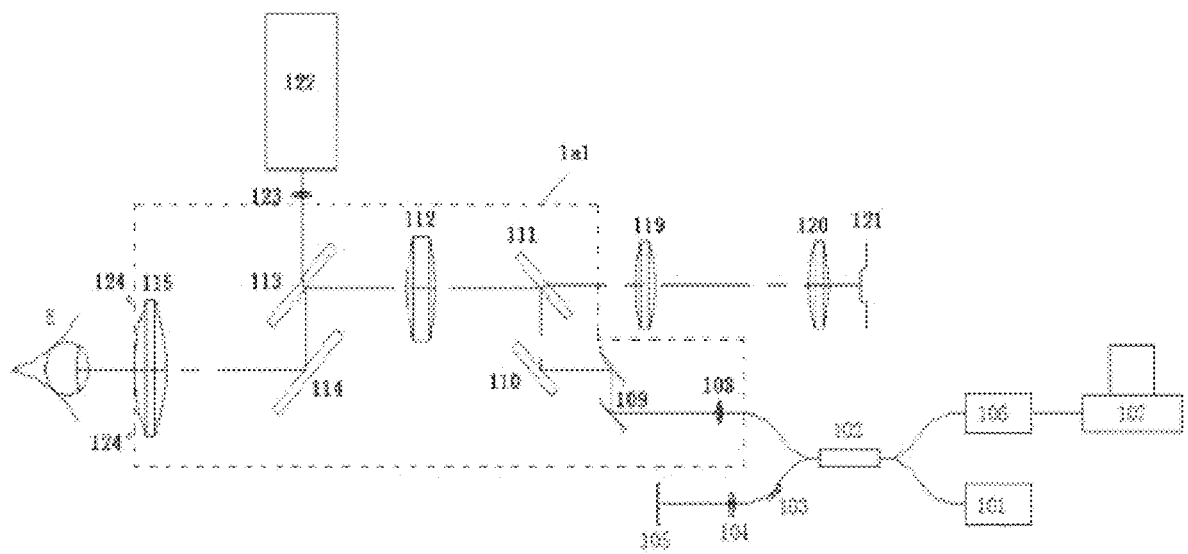
FIG. 3 is the first optical path system diagram of the OCT system in patent CN102438505ZHONG.
Figure 4:
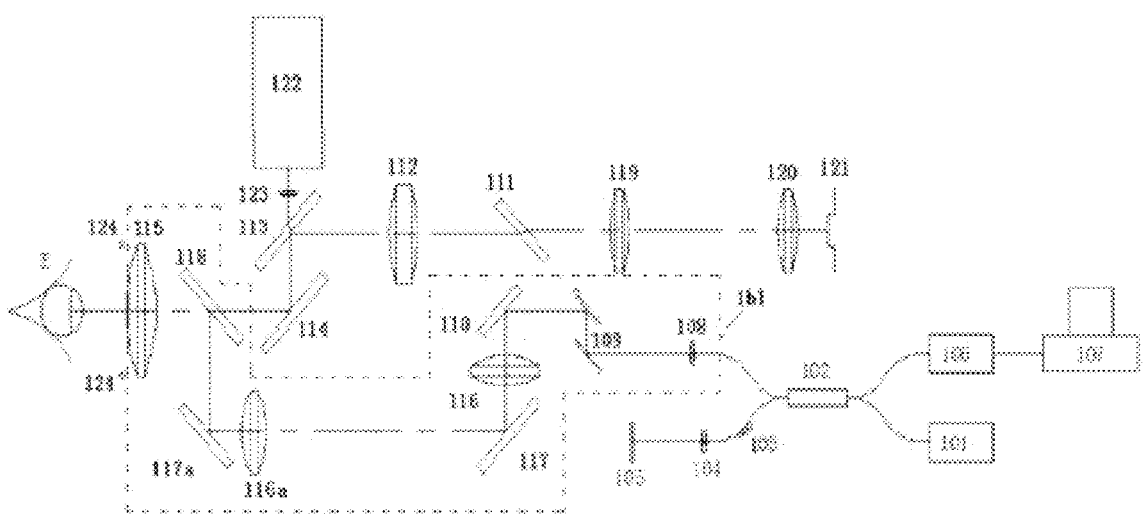
FIG. 4 is the optical path system diagram of the OCT system in patent CN102438505ZHONG.
Figure 5:
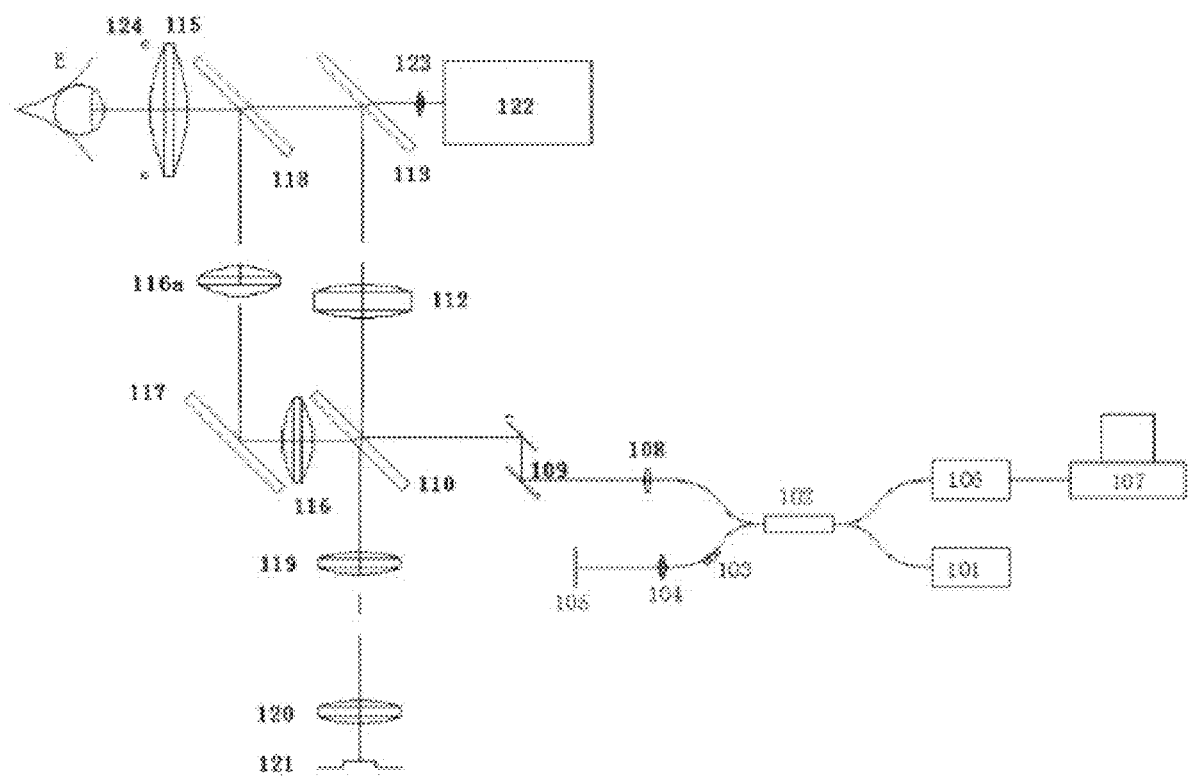
FIG. 5 is the third optical path system diagram of the OCT system in patent CN102438505ZHONG.
Figure 6:
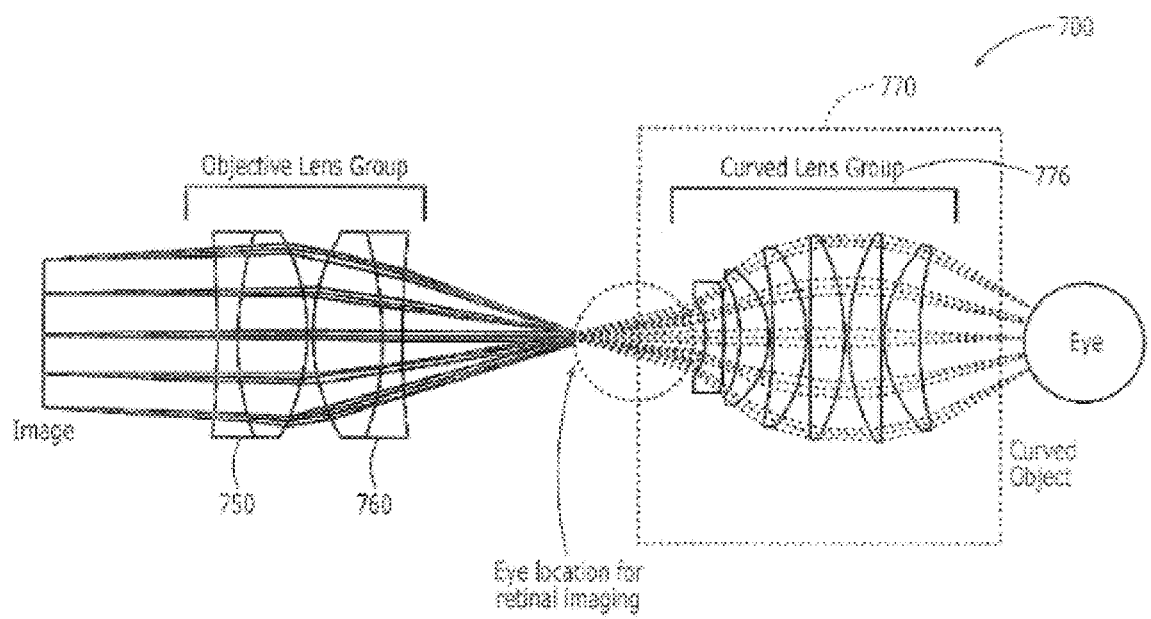
FIG. 6 is a lens schematic diagram of the sample arm of an OCT system in patent US2008/0106696A1.

The present invention will be described in detail below with reference to specific embodiments.

The present invention is an ophthalmic imaging system. It provides an internal switching method which is easy to operate. Considering different diopters of eyes to image, refractive adjustment is required in both retina and anterior segment imaging modes in order to ensure proper focus. In the present invention, switching is contained within the OCT optical path, and the optical paths of other auxiliary subsystems are not affected in the switching process.

The ophthalmic OCT system described in the embodiments of the present invention includes an OCT imaging module, a scanning laser ophthalmoscope (SLO) imaging module, an anterior segment imaging module and a fixation target module. Working wavelengths of the imaging modules are different. By employing a group of dichroic mirrors, imaging and illumination functions of each waveband are realized.

The technical problems to be solved by the embodiments of the present invention are as follows. First, an ophthalmic imaging system that incorporates both OCT imaging modes of retina and anterior segment and a switching method between the foresaid two imaging modes thereof are provided. Other auxiliary positioning functions can be ensured in the process of switching between the aforementioned imaging modes, while other imaging functions are not affected, namely, imaging functions of the pupil camera module, the retina SLO module and the fixation module are not affected. Second, after switching from the retina OCT mode to the anterior segment OCT mode, a second intermediate image is formed in the optical path inside the switching lens group and a conjugate of the entrance pupil forms near the back focal plane of the ocular lens. The said design makes the imaging of anterior segment telecentric or near telecentric. It also makes it more flexible to control the angle of the light entering the anterior segment and improve the achievable field of view and imaging resolution.

The ophthalmic imaging system includes a retina OCT imaging mode and an anterior segment OCT imaging mode. Switching from the retina imaging mode to the anterior segment imaging mode is realized by switching a subset of or all of the lenses of the OCT imaging module. The OCT imaging module comprises all of the non-planar optical elements between the ocular lens and the galvanometer. The OCT imaging module is switched from one mode to another mode through movement of a lens group in the OCT optical path. Compared with the retina imaging mode, the anterior segment imaging mode contains a new intermediate image plane in the OCT imaging module, and the position of the intermediate image plane is different from that of the retina imaging mode.

In both of the OCT retina imaging mode and the anterior segment imaging mode, the theoretical position of the OCT galvanometer is positioned at the entrance pupil of the OCT imaging module. The switching of the retina and the anterior segment is actually the switching of the approximate image plane and the pupil plane. In the present invention, the position of the intermediate image plane in the OCT retina imaging mode is the approximate conjugate position of the entrance pupil in the anterior segment imaging mode, that is, the image plane is switched to the pupil plane.

In the retina imaging mode, the entrance pupil of the OCT imaging module and the eye pupil form a pair of conjugates, and the galvanometer is positioned at the entrance pupil. In the anterior segment imaging mode, the position of the entrance pupil remains unchanged but it is not a conjugate of the eye pupil any more. Instead, a conjugate of the entrance pupil is formed between the ocular lens and the OCT imaging module, on or near the back focal plane of the ocular lens, as a result, the light incident on the eye is parallel or nearly parallel thus achieving telecentric or nearly telecentric imaging of the anterior segment.

In the switching process, no planar optical elements move or change in position or direction, there is no need to add or reduce reflectors or other planar optical elements in the optical path.

The optical design of this invention ensures that optical lengths of the sample arm are approximately the same before and after switching between the retina imaging mode and the anterior segment imaging mode, and therefore, minimizes the movement range of the reference arm needed to compensate the difference of optical path lengths of the two imaging modes.

When the ophthalmic imaging system performs retina imaging, near-infrared rays reach a galvanometer, then sequentially pass through the OCT retina imaging module and the ocular lens, and are focused on the retina. The light reflected and scattered by the retina returns to the galvanometer along the way it comes. The imaging optical path is characterized in that an intermediate imaging plane exists between the OCT retina imaging module and the ocular lens, and the intermediate imaging plane is approximately telecentric.

When the ophthalmic imaging system performs anterior segment imaging, near-infrared rays pass through the galvanometer, then sequentially pass through the OCT imaging module configured in anterior segment imaging mode, and the ocular lens, and are focused on the anterior segment. The light reflected and scattered by the anterior segment returns to the galvanometer along the way it comes. The imaging optical path is characterized in that: firstly, the position of the intermediate image plane in the retina imaging mode becomes the approximate conjugate position of the entrance pupil in the anterior segment imaging mode; secondly, compared with the retina imaging module, the anterior segment imaging module creates an intermediate image plane inside the switching lens group; and thirdly, there is at least one negative power lens near the said intermediate image plane of OCT anterior segment module.

Figure 13:
FIG. 13 is an OCT image on a healthy retinal obtained by the OCT imaging system of the present invention.
Figure 14:
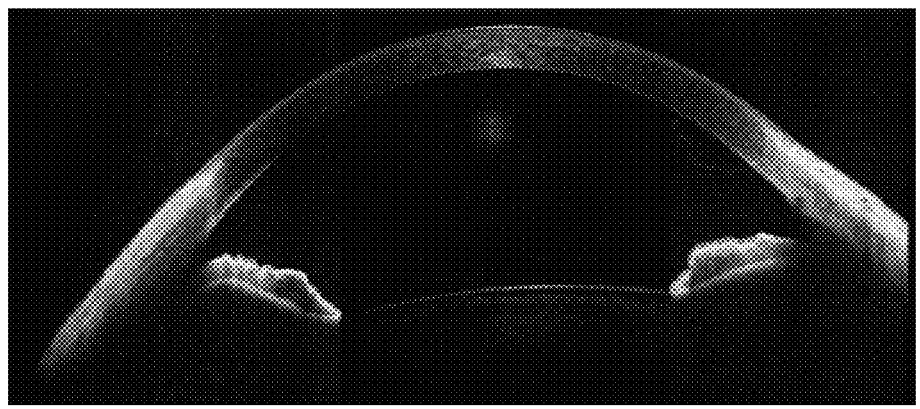
FIG. 14 is an OCT image on a healthy anterior segment obtained by the OCT imaging system of the present invention

OCT images of the retina and the anterior segment of a healthy eye, taken from an ophthalmic imaging system based on this invention, are shown in FIGS. 13 and 14 respectively. The SLO module in the ophthalmic imaging system is an auxiliary imaging module to image the retina, wherein a near-infrared scanning light in a waveband different from OCT waveband passes through the SLO galvanometer, the SLO imaging module and the ocular lens sequentially and is focused on the retina. The light reflected and scattered by the retina returns to the SLO scanning galvanometer along the way it comes.

The ophthalmic imaging system with the aforementioned switching method between retina and anterior segment is further materialized in mechanical design.

Figure 15:
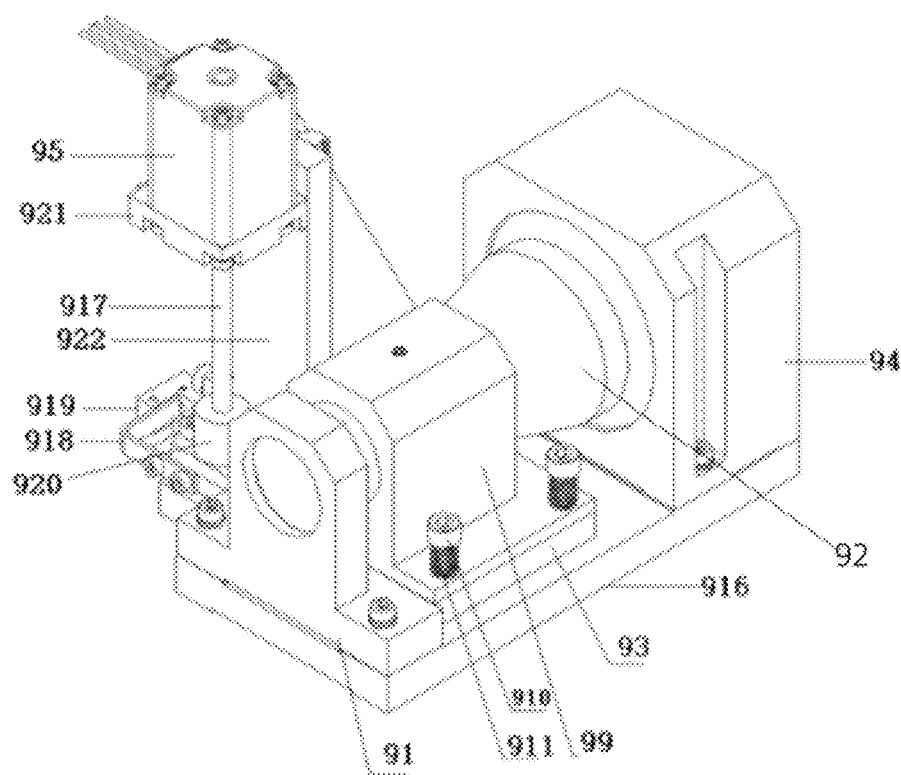
FIG. 15 is a schematic structural diagram (View Angle I) of the lens group switching device in the OCT imaging system of the present invention.

As shown in FIG. 15, the ophthalmic imaging system of the present invention further includes a lens group switching device, and the switching movement of the switching lens group assembly 99 is realized by the lens group switching device. The lens group switching device switches the switching lens group assembly 99 to form two imaging modes, namely the retina OCT imaging mode and the anterior segment OCT imaging mode.

Figure 16:
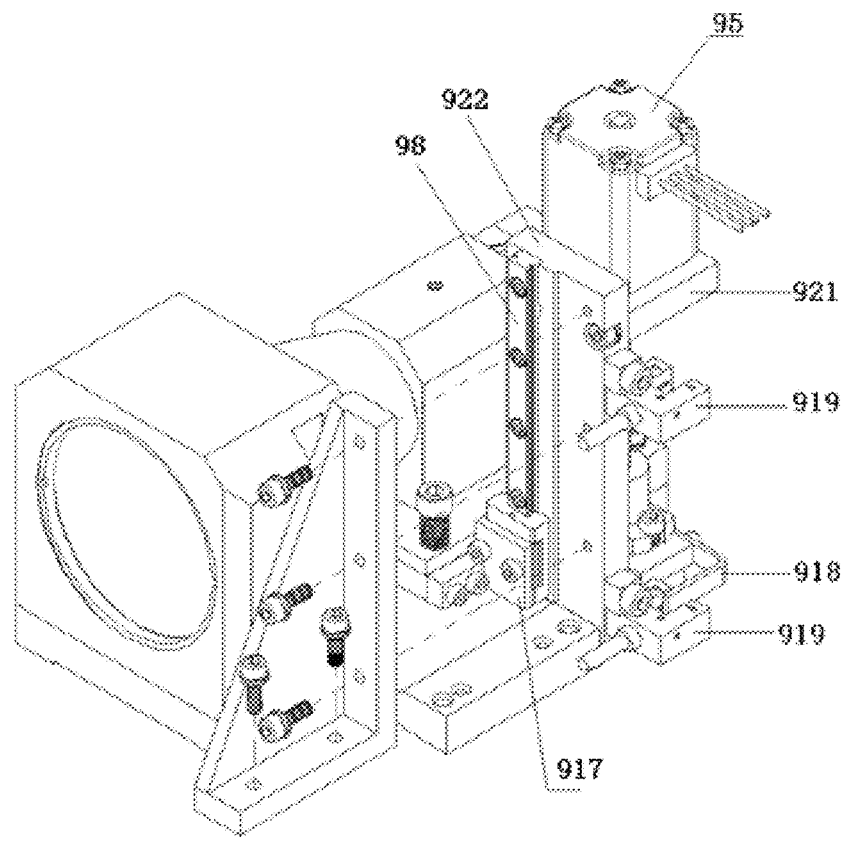
FIG. 16 is a second schematic structural diagram (View Angle II) of the lens group switching device in the OCT imaging system of the present invention.

As shown in FIGS. 15 and 16, the lens switching device includes a base plate 916 and a driving platform vertically fixed on the base plate 916. The front lens group 94 and the rear lens group 91 are both mounted on the based plate 916. The switching lens group 92 is embedded on the base plate 916 through a positioning block located between the front lens group 94 (Lenses 11, 12 in FIG. 9; Lenses 21, 22 in FIG. 12) and the rear lens group 91 (Lens 13 in FIG. 9; Lens 23 in FIG. 12). The lens group switching device further includes a driving motor 95, and a ball screw 917 connected with a rotating shaft of the driving motor 95 is fixed on a horizontal part 921 of the driving platform. The ball screw 917 passes through a feed screw nut 920 and a prepressing plate 93 and then is fixed on the base plate 916. A guide rail is fixed on a vertical part 922 of the driving platform. The vertical part 922 of the driving platform is equipped with two photoelectric sensors 919 in the longitudinal direction. The switching lens group assembly includes the switching lens group 92 and switching lens mount 99. The prepressing plate 93 elastically (flexibly) is connected with the switching lens mount 99. The feed screw nut 920 is connected with the matching ball screw 917.

As shown in FIG. 16, a slider 917 capable of moving up and down along the guide rail 918 are fixed on the prepressing plate 93. A triggering part 918 to trigger the photoelectric sensors 919 is also connected with the prepressing plate 93. The lens switching device further includes a system controller, and the driving motor 95 and the photoelectric sensors 919 are both connected to the system controller.

Also shown in FIG. 16, photoelectric sensors 919 are configured to identify the position of the switching lens group 92. The photoelectric sensors are triggered by the triggering part 918 fixed on the switching lens group assembly. When the photoelectric sensors on the upper portion of the vertical part 922 of the driving platform is triggered, that is, when the receiver of the photoelectric sensor 919 is blocked by the triggering part 918 and stops receiving the laser light from the transmitter, that is, the upper photoelectric sensor 919 sends a signal to the system controller, which then acknowledges that the switching lens group 92 is not in the OCT light path and the OCT imaging system is in the retina imaging mode. When the photoelectric sensor on the lower portion of the vertical part 922 of the driving platform is triggered, similarly, the lower photoelectric sensor sends a signal to the system controller, which then acknowledges that the switching lens group 92 is in the OCT light path and the OCT imaging system is in the anterior segment imaging mode.

Figure 21:
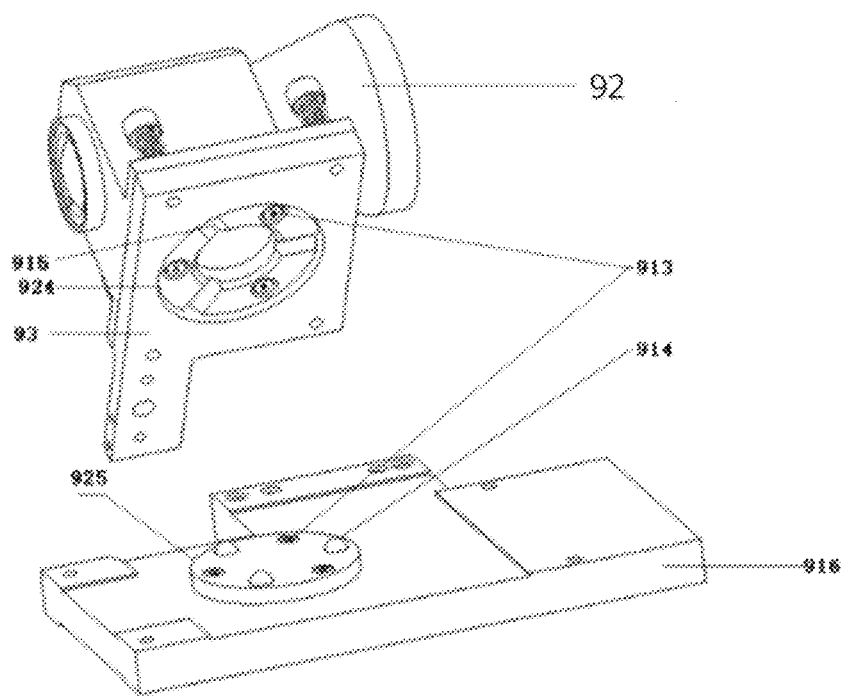
FIG. 21 is a schematic diagram of combination of the switching lens group assembly and the base plate.

The positioning precision of the switching lens group assembly is guaranteed by a kinetic interface between the prepressing plate 93 and the base plate 916. As shown in FIG. 21, the bottom of the prepressing plate 93 has an annular positioning area 924. Three magnets 913 are equidistantly mounted on the annular positioning area 924. There is a V-shaped groove 915 between each pair of the adjacent magnets 913. The three V-shaped grooves 915 are also equidistantly positioned in the annular positioning area 924. The base plate 916 also has an annular positioning part 925. Three magnets 913 are equidistantly mounted on the annular positioning part 925. There is a steel ball 914 between each pair of the adjacent magnets 913. The three semicircular steel balls 914 are also equidistantly positioned in the annular positioning part 925. The magnets 913 at the bottom of the prepressing plate 93 and on the base plate 916 are arranged correspondingly. The semicircular steel balls 914 are in kinetic contact with the V-shaped grooves 915 when the switching lens group assembly is switched onto the base plate 916.

The main purpose of the lens group switching device is to ensure that the optical axis of the switching lens group 99 is coaxial with the existing optical axis of the OCT imaging system. When the switching lens group 99 moves out of the main optical path, the OCT imaging system is in the retina imaging mode. When it is moves into the main optical path, the OCT imaging system is in the anterior segment imaging mode.

Figure 17:
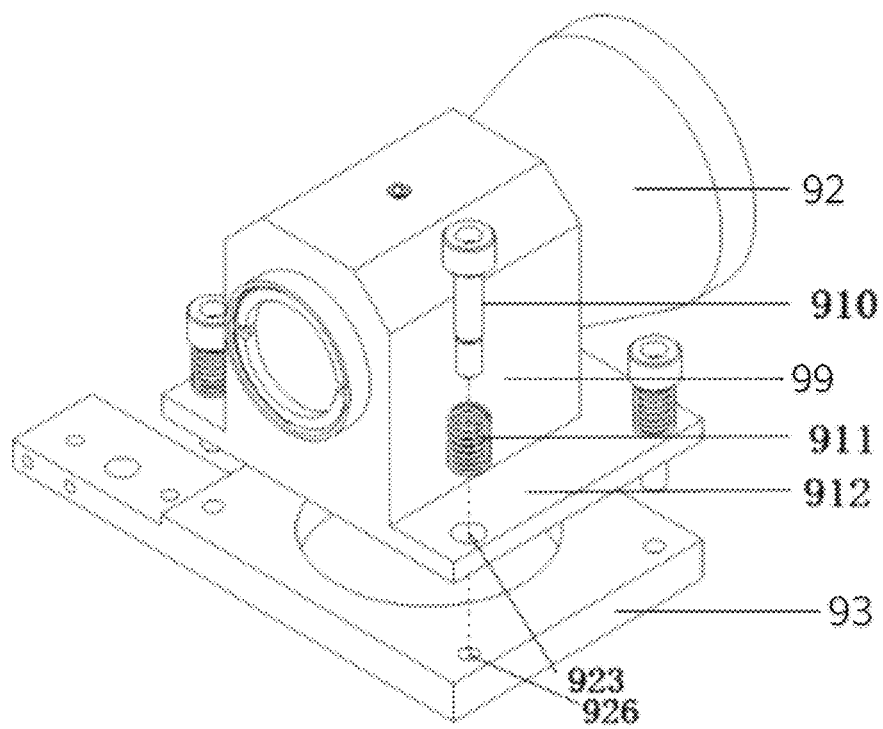
FIG. 17 is an exploded view of the switching lens group assembly and the prepressing plate.
Figure 18:
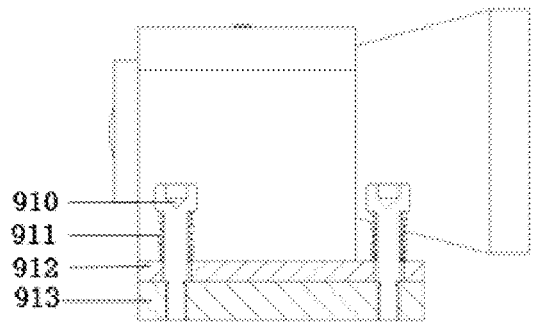
FIG. 18 is an elementary diagram of combination of the switching lens group assembly and the prepressing plate.

As shown in FIGS. 17 and 18, the bottom part 912 of the switching lens mount 99 has a set of through holes 923. The prepressing plate 93 has a set of threaded holes 926 matching the through holes 923. The switching lens mount 99 and the prepressing plate 93 are connected through connecting screws 910. The connecting screws 910 are sheathed in springs 911. The connecting screws 910 sequentially pass through the springs 911 and the through holes 923 and are connected with the threaded holes 926 by threads. The switching lens mount 99 is pressed against the prepressing plate 93 by a pre-tightening force (FIG. 19) provided by four sets of the connecting screws 910 and the springs 911. Therefore, although the switching lens mount 99 is connected to the prepressing plate 93, the springs 911 help to preserve flexibility and there is still flexibility between the said two parts, that is, they are in elastic connection to prevent excessive positioning error caused by over-constraint on the switching lens group 92.

Figure 20:
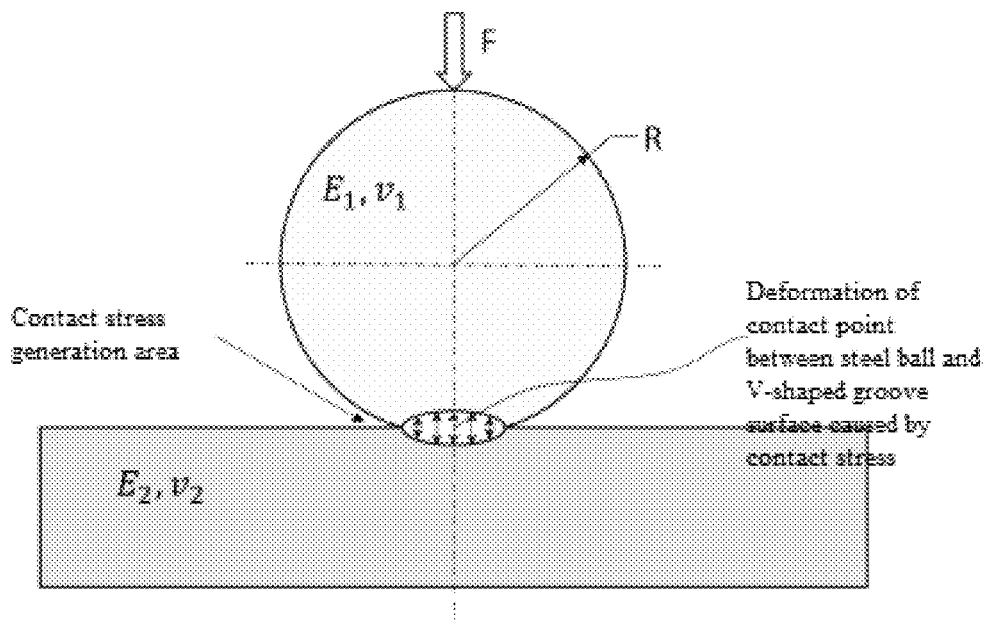
FIG. 20 is a schematic diagram of stress deformation caused by contact stress.

As shown in FIG. 20, the positioning module in the lens group switching device uses three precision steel balls 914 and three matching V-shaped grooves 915 to constrain five degrees of freedom of the switching lens mount 99 and the base plate 916. The pre-tightening force constrains the sixth degree of freedom. In this way, the precise positioning of the switching lens group 92 with respect to the base plate 916 is realized.

Figure 19:
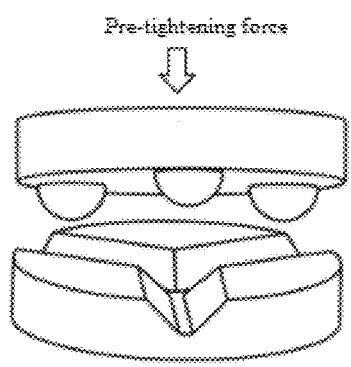
FIG. 19 is an elementary diagram of combination of the positioning module.

The deformation of the spherical surface of the steel balls and the surface of the V-shaped groove is calculated as follows (as illustrated in FIGS. 19 and 20):

$$\delta_s = 1.04 \left[ F \left( \frac{1-v_1^2}{E_1} + \frac{1-v_2^2}{E_1} \right) \right]^{\frac{2}{3}} \left[ \frac{1}{2} \left( \frac{1}{R} \right) \right]^{\frac{1}{3}}, \quad (1)$$

where
$\delta_s$ is the deformation of the spherical surface of the steel balls and the surface of the V-shaped groove,
R is the radius of the steel balls,
$E_1$ is the elastic modulus of the steel,
$v_1$ is the Poisson ratio of the steel,
$E_2$ is the elastic modulus of the material of the V-shaped grooves;
$v_2$ is the Poisson ratio of the material of the V-shaped grooves, and
F is the load on the steel balls.

As shown in FIG. 21, three pairs of small cylindrical magnets 913 provide the pre-tightening force. The load on the steel balls 914 is provided by the three pairs of small cylindrical magnets 913, and the magnetic force provided by each pair of magnets 913 is 3 N. Assuming the weight of the switching lens group assembly is 4.5 N. Therefore, the total load $F_{total}$ on each steel ball 914 is 4.5 N.

Figure 22:
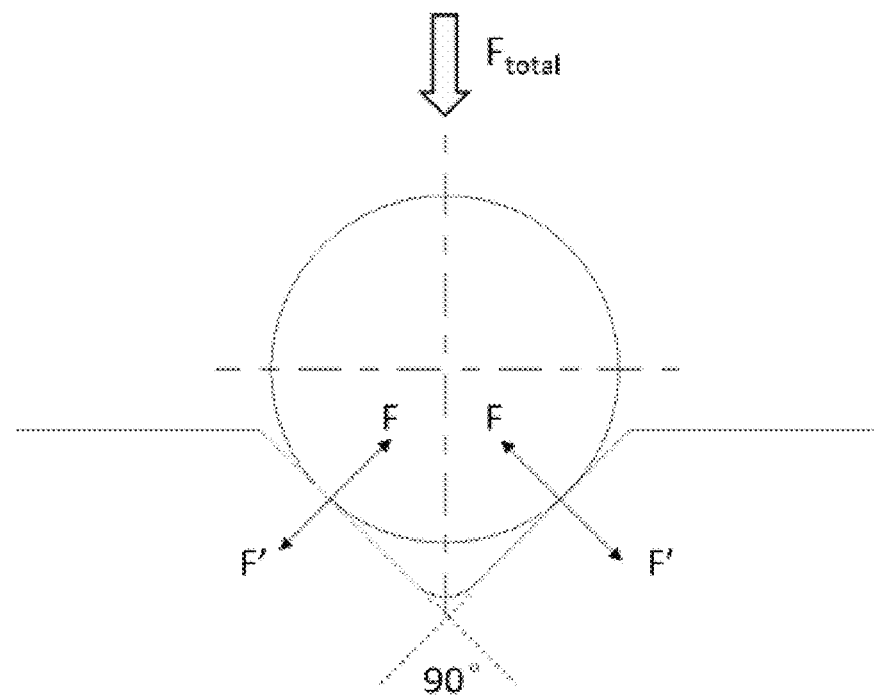
FIG. 22 is an elementary diagram of force analysis of one of the steel balls.

Therefore, as shown in FIG. 22, the contact load F between the steel ball and the V-shaped groove surface is calculated as follows:

$$\sin 45° = \frac{F}{F_{TOTAL}}, \text{ and}$$

$$F = 4.5N \times \frac{\sqrt{2}}{2} \approx 3.2N.$$

The steel ball is made of stainless steel and the material properties thereof are:
R=4 mm,
$E_1 = 210 \times 10^9$ pa, and
$v_1 = 0.28$.

The material of the V-shaped groove is aluminum alloy AL6061, and the material properties thereof are:
$E_2 = 82 \times 10^9$ pa, and
$v_2 = 0.206$.

The above parameters are substituted into the deformation equation (1) to obtain:
$\delta_s \approx 0.72$ μm.

According to the calculation, the repetition precision of the lens group switching device in the present invention can be controlled at micron level.

The lens group switching device can ensure high positioning precision of the components in the optical instrument under repetitive switching. The coaxiality precision is +/−0.03 mm, and the tilting accuracy 2'. The lens group switching device is sufficient to maintain positioning tolerance of the switching components required by the optical design during each switching and after repetitive switching, and the image quality can still meet the design target.

Figure 23:
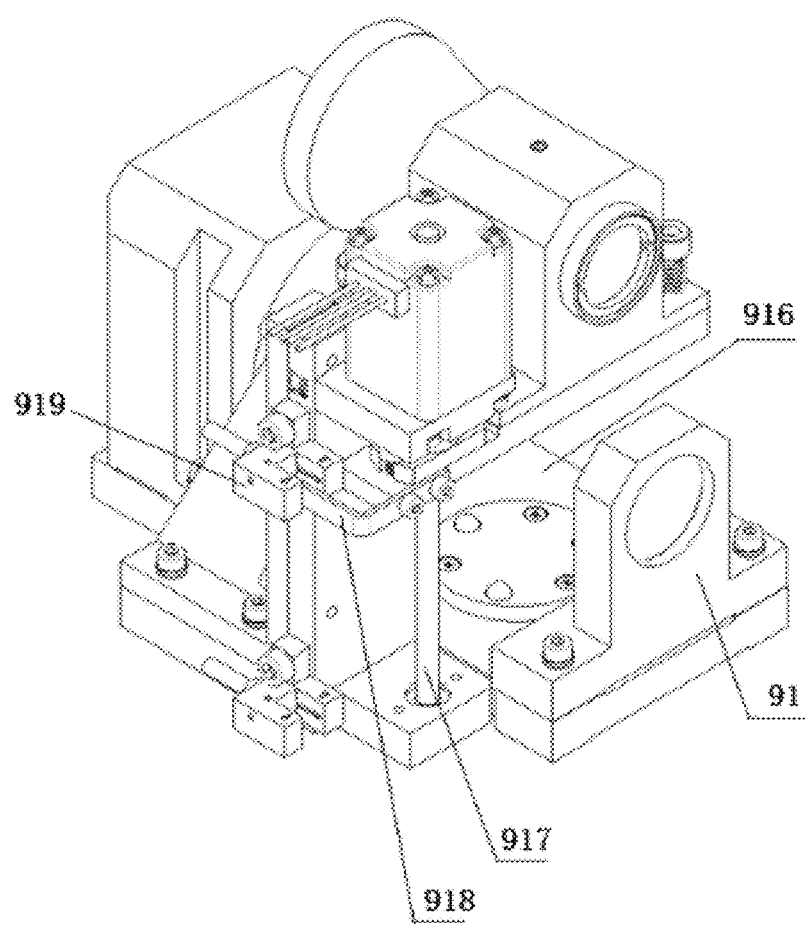
FIG. 23 is a schematic structural diagram of the lens group switching device of the present invention in the retina testing mode.
Figure 24:
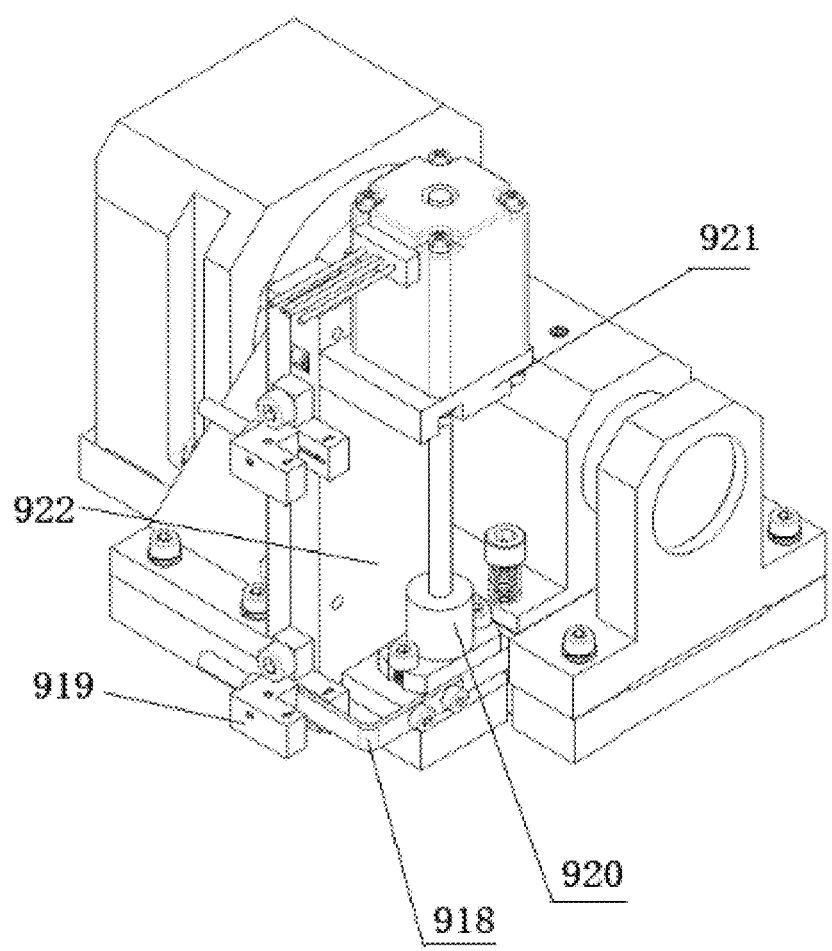
FIG. 24 is a schematic structural diagram of the lens group switching device of the present invention in the anterior segment testing mode.

FIGS. 13 and 14 are exemplary images obtained by an ophthalmic imaging system built based on the present invention, in the retina OCT imaging mode (FIG. 23) and the anterior segment imaging mode (FIG. 24), respectively.

Embodiment 1

Figure 7:
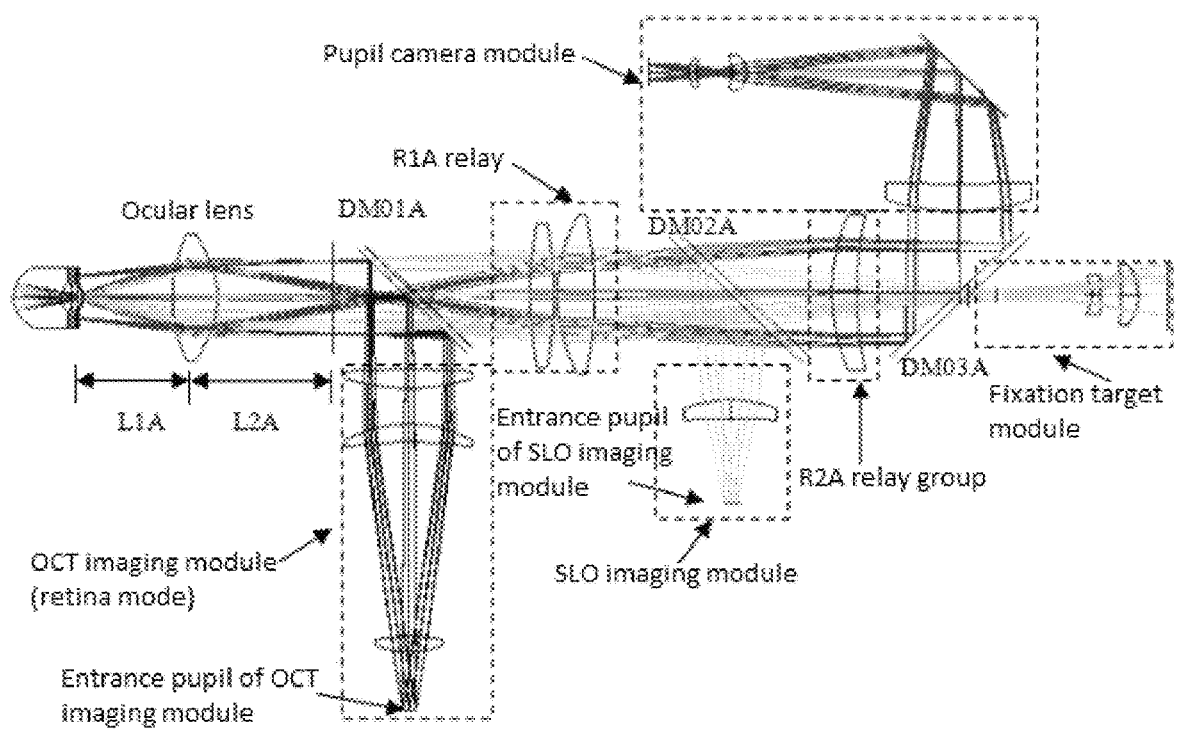
FIG. 7 is an optical path system diagram of the first embodiment of the present invention.

As shown in FIG. 7, in the ophthalmic imaging system, the OCT imaging module, the SLO imaging module, the pupil camera module and the fixation target module share one ocular lens. The working distance L1A between the ocular lens and the human eye to be tested can be adjusted to facilitate focusing of the pupil camera module. The distance L2A from the back of the ocular lens to the first dichroic mirror DM01 can be adjusted to compensate the refractive difference of human eyes for up to +/−20 diopters.

In the ophthalmic imaging system, as shown in FIG. 7, the OCT imaging module and the SLO imaging module are both located on the same side of a line where a visual axis of the eye is located, and the pupil camera module is on the opposite side. The advantage of the present embodiment is that the SLO imaging module passes through only one dichroic mirror, and results the lowest impact on the image quality.

In the present embodiment, optical path division between the OCT imaging module and other functional modules is achieved by a dichroic mirror DM01A of long wave reflection and short wave transmission. The relay group R1A is a lens group shared by the SLO imaging module, the pupil camera module and the fixation module. Optical path division among the SLO imaging module, the pupil camera module and the fixation module is achieved by a dichroic mirror DM02A of long wave reflection and short wave transmission. The relay group R2A is a lens group shared by the pupil camera module and the fixation module. Optical path division between the pupil camera module and the fixation module is achieved by a dichroic mirror DM03A of long wave reflection and short wave transmission.

Figure 9:
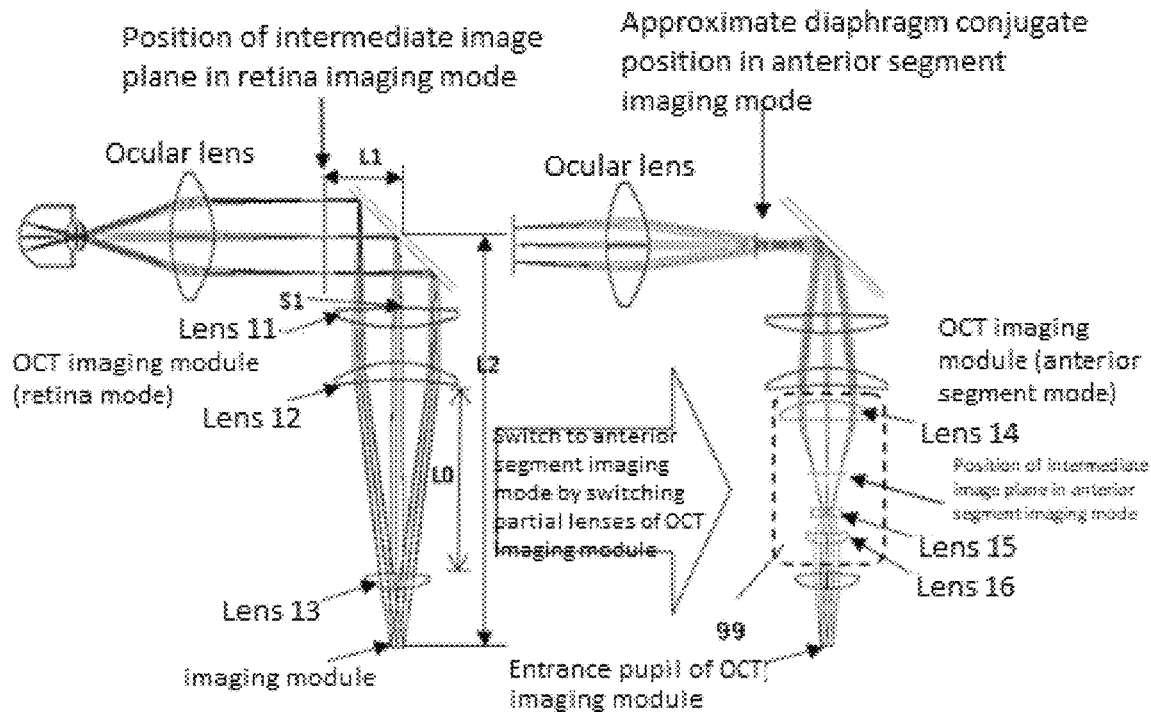
FIG. 9 is an optical path system diagram of OCT path in the first embodiment of the present invention, in which by switching part of the OCT lenses (enclosed by the dash line box), the OCT imaging system switches between retina imaging mode (left: without switching lens group) and anterior segment imaging mode (right: with switching lens group).
Figure 10:
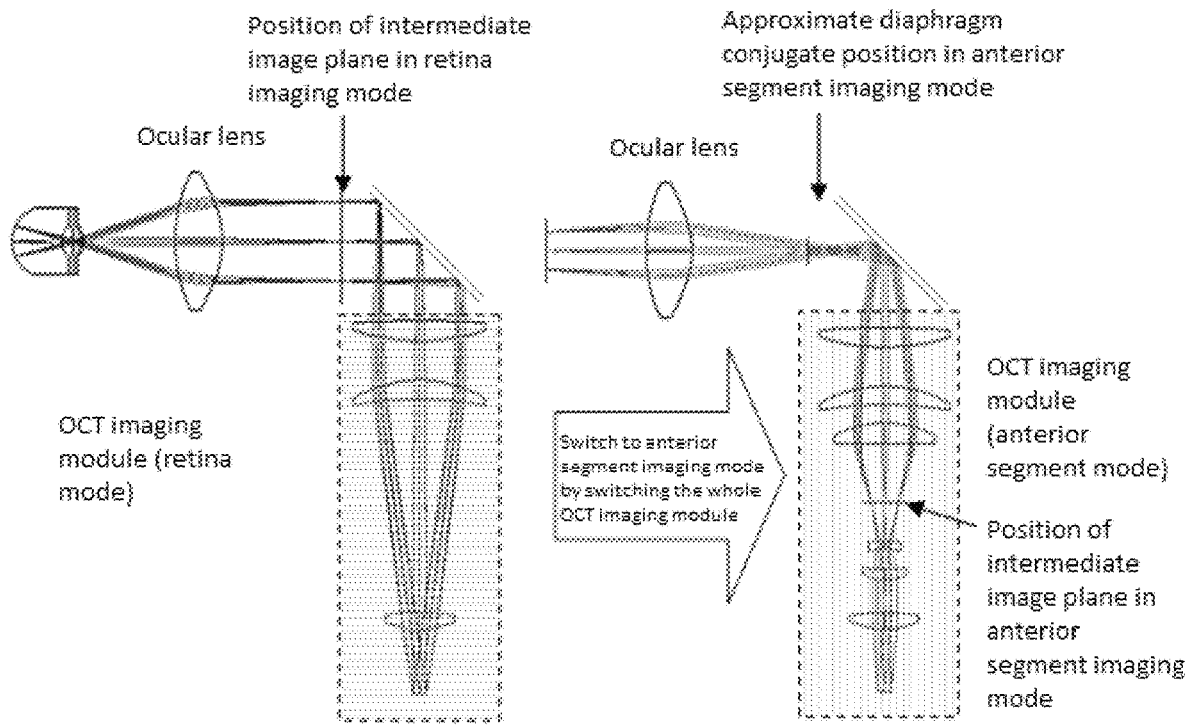
FIG. 10 is an optical path system diagram of OCT path in the first embodiment of the present invention, in which by switching all elements of the OCT lens group (enclosed by the dash line box), the OCT imaging system switches between retina imaging mode (left: without switching lens group) and anterior segment imaging mode (right: with switching lens group)

In the present embodiment, the OCT imaging module shown in FIG. 7 is in retina imaging mode. The switching between the retina imaging mode and the anterior segment imaging mode can be accomplished by switching a subset of the lenses of the OCT imaging module. As shown in FIG. 9, the switching of the lenses is realized by the lens group switching device of the present invention. The switching between the OCT retina imaging mode and the anterior segment imaging mode can also be accomplished by switching all of the lenses of the OCT imaging module, as shown in FIG. 10.

The imaging module in the retina imaging mode in FIG. 9 is composed of a first lens 11, a second lens 12, and a third lens 13. The first lens 11 is a biconvex lens. The S1 plane becomes the one closest to the approximate diaphragm conjugate after switching to the anterior segment imaging mode. If the S1 surface is designed to be planar, it will tend to generate stray light ghosting so the radius of the S1 surface is constrained to be less than 300 mm during the optical design. The second lens 12 is a meniscus lens of which both surfaces are bent toward the OCT galvanometer. The third lens 13 is a biconvex lens. It is the closest to the OCT galvanometer, and the distance $L_0$ between the second lens 12 and the third lens 13 provides space for the switching lens. $L_0$ satisfies the following constraint conditions:

$$0.4 < \left| \frac{L_0}{L_1 + L_2} \right| < 0.7,$$

where $L_1$ is the distance between the first intermediate image plane and the center of the first dichroic mirror, and $L_2$ is the distance between on the center of the first dichroic mirror and the galvanometer.

The imaging module in the anterior segment imaging mode in FIG. 9 includes a fourth lens 14, a fifth lens 15, and a sixth lens 16 in addition to the aforementioned lenses 11-13. The fourth lens 14 is a near-plano-convex lens. The near-plano surface is on the side near the intermediate image plane of the anterior segment, and the center of the convex surface is on the side of the OCT galvanometer. On the other side near the intermediate image plane, a negative power fifth lens 15 is added for field curvature compensation. The negative power fifth lens 15 is between the intermediate image plane and the OCT galvanometer. The sixth lens 16 close thereto is a positive lens and a meniscus lens, and the centers of two surfaces are both on the side away from the OCT galvanometer.

Embodiment 2

Figure 8:
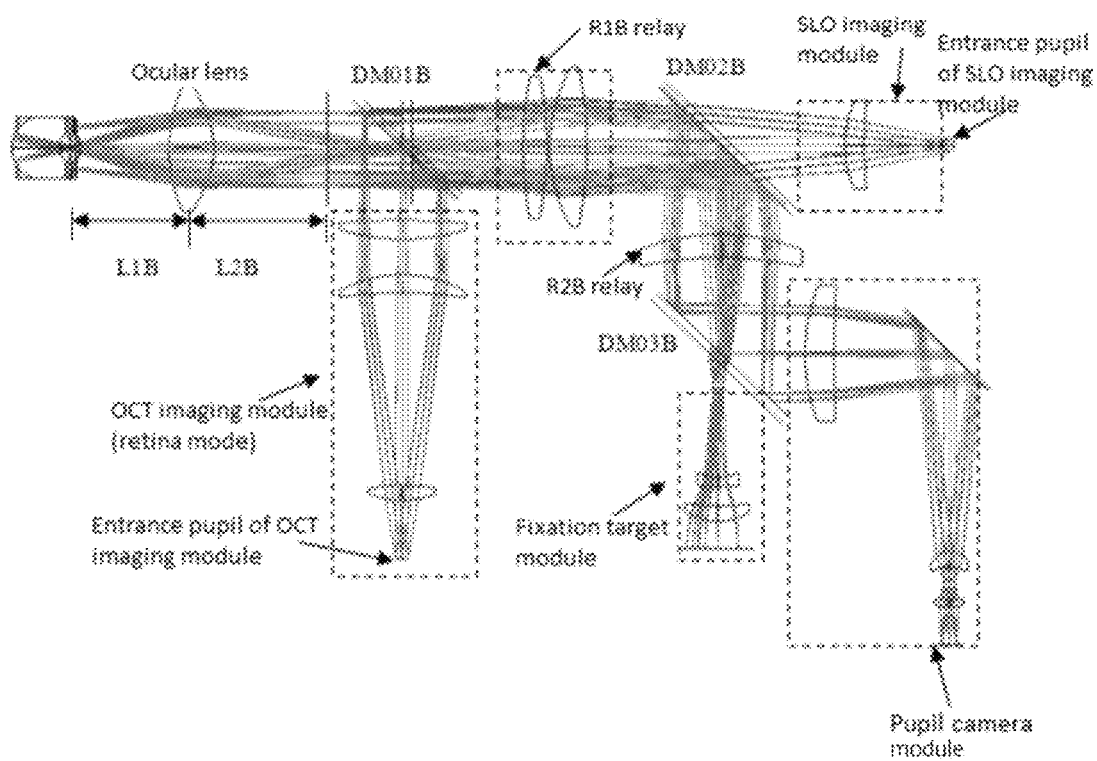
FIG. 8 is an optical path system diagram of the second embodiment of the present invention.

As shown in FIG. 8, in the ophthalmic imaging system, the OCT imaging module, the SLO imaging module, the pupil camera module and the fixation target module share one ocular lens. The working distance L1B between the ocular lens and the human eye to be tested can be adjusted to facilitate the focusing of the anterior segment imaging system. The distance L2B from the back of the ocular lens to the first dichroic mirror DM01 can be adjusted to compensate for the refractive difference of human eyes.

In the ophthalmic imaging system, as shown in FIG. 8, the OCT imaging module, the fixation module and the pupil camera module are all located on the same side of the line where the visual axis of the eye. The DM02B is a dichroic mirror of long wave transmission and short wave reflection and more readily available as a catalog product than the opposite. In the present embodiment, optical path division between the OCT imaging module and other functional modules is achieved by a dichroic mirror DM01B of long wave reflection and short wave transmission. Relay group R1B is a lens group shared by the SLO imaging module, the pupil camera module and the fixation module. Optical path division among the SLO imaging module, the pupil camera module and the fixation module is achieved by a dichroic mirror DM02B of long wave transmission and short wave reflection. The relay group R2B is a lens group shared by the pupil camera module and the fixation module. Optical path division between the pupil camera module and the fixation module is achieved by a dichroic mirror DM03B of long wave reflection and short wave transmission.

Figure 11:
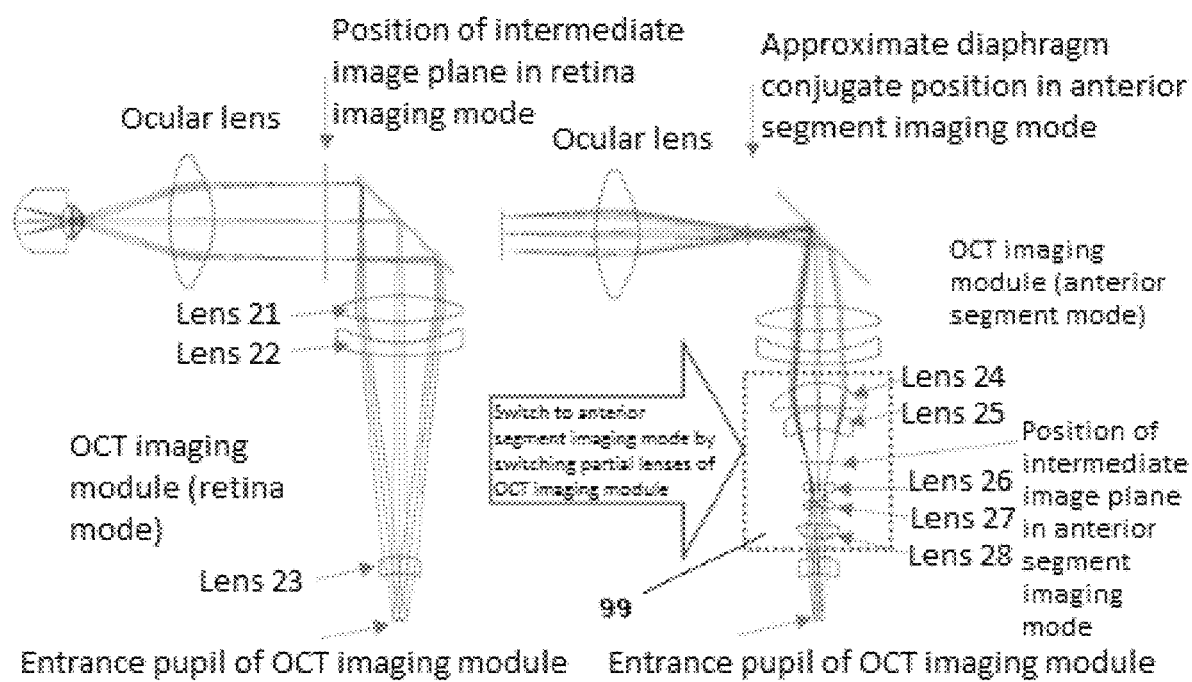
FIG. 11 is an optical path system diagram of OCT path in the second embodiment of the present invention, in which by switching part of the OCT lenses (enclosed by the dash line box), the OCT imaging system switches between retina imaging mode (left: without switching lens group) and anterior segment imaging mode (right: with switching lens group)

As shown in FIG. 11, the OCT imaging module in the retina imaging mode is composed of a first lens 21, a second lens 22 and a third lens 23. The first lens 21 is a biconvex positive lens. The second lens 22 is a meniscus lens to balance field curvature, and the centers of both surfaces of the second lens are on the side away from the OCT galvanometer. The third lens 23 is also a meniscus lens, and the centers of both surfaces of the third lens are on the side close to the OCT galvanometer.

The imaging module in the OCT anterior segment imaging mode in FIG. 11 includes a second fourth lens 24, a second fifth lens 25, a second sixth lens 26, a seventh lens 27, and an eighth lens 28 in addition to the aforementioned lenses 21-23. The second fourth lens 24 and the second fifth lens 25 are meniscus lenses, and the centers of the surfaces of the second fourth lens and the second fifth lens are on the side near the intermediate image plane in the anterior segment imaging mode. The second sixth lens 26 is a biconcave negative lens and the second seventh lens 27 is a meniscus lens, both of which compensate field curvature near the intermediate image plane. The second eighth lens 28 is a biconvex positive lens next to the OCT galvanometer.

Figure 12:
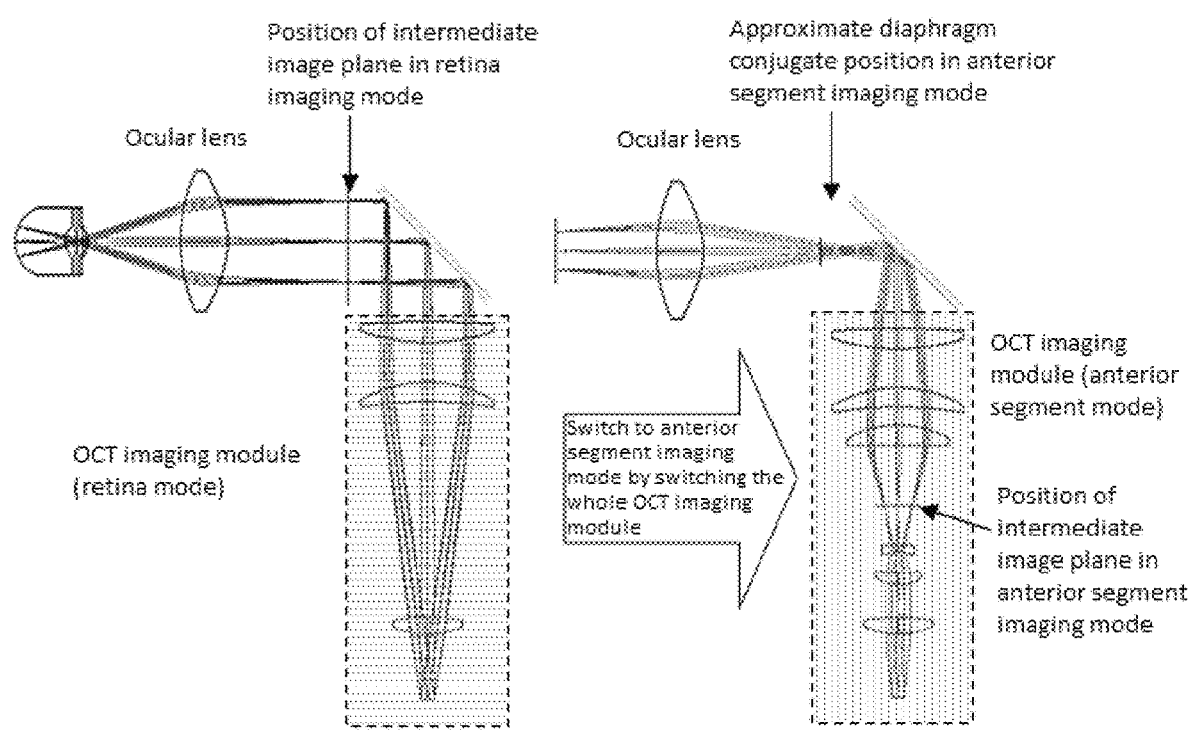
FIG. 12 is an optical path system diagram of OCT path in the second embodiment of the present invention, in which by switching all elements of the OCT lens group (enclosed by the dash line box), the OCT imaging system switches between retina imaging mode (left: without switching lens group) and anterior segment imaging mode (right: with switching lens group)

In the present embodiment, the OCT imaging module shown in FIG. 8 is a retina imaging mode, and the switching between the retina imaging mode and the anterior segment imaging mode can be accomplished by switching a subset of the lenses of the OCT imaging module. As shown in FIG. 11, the switching of the lenses is realized by the lens group switching device in the present invention. The switching between the OCT retina imaging mode and the anterior segment imaging mode can also be accomplished by switching all of the lenses of the OCT imaging module, as shown in FIG. 12.

In both embodiments, when switching to the OCT anterior segment imaging mode from retina imaging mode, an intermediate image plane will be presented in the OCT imaging module. The position of the intermediate image plane is different from that of the retina imaging mode. The position of the intermediate image plane in the retina imaging mode is approximately the back focal plane of the ocular lens. In the anterior segment imaging mode, the conjugate of the entrance pupil also falls in that position, so the light incident on the eye is approximately parallel to the optical axis, achieving telecentric imaging of the anterior segment. While switching between retina and anterior segment scanning modes of the OCT module, the imaging and illumination optical paths of other modules in the system, such as the SLO module, the anterior segment imaging module and the fixation target module, are not affected. No planar optical elements move or change in position or direction. There is no need to add or reduce reflectors or other planar optical elements in the optical path.

In both embodiments, the optical design ensures that the optical path lengths of the sample arm remain approximately the same before and after switching. Specifically, the optical path ratio of the retina imaging mode and the anterior segment imaging mode of the OCT imaging module satisfies the following formula:

$$0.9 \leq \frac{OPL_{retina}}{OPL_{cornea}} \leq 1.1,$$

wherein $OPL_{retina}$ represents the optical path length of the retina imaging mode measured from the entrance pupil of the OCT imaging module to the retina of a standard human eye, and $OPL_{cornea}$ represents the optical path length of the anterior segment imaging mode measured from the entrance pupil of the OCT imaging module to the iris of a standard human eye. With the said design, the necessary moving range of the reference arm does not have to increase much due to the switching.

The above are only preferred embodiments of the present invention and are not intended to limit the present invention. All modifications, equivalent substitutions and improvements made within the theories, essences, solutions and principles of the present invention are within the scope of protection of the present invention.

What is claimed is:

1. An ophthalmic imaging system, comprising an ocular lens and an optical coherence tomography (OCT) imaging module, wherein the OCT imaging module comprises a retina imaging mode and an anterior segment imaging mode;
    in the retina imaging mode, the ophthalmic imaging system includes a first intermediate image plane located between the ocular lens and the OCT imaging module; and
    from the retina imaging mode, an anterior segment imaging via the anterior segment imaging mode is achieved by inserting a switching lens group into the optical path between the entrance pupil of the OCT imaging module and the first intermediate image, wherein, after the insertion, the OCT imaging module includes a second intermediate image plane located inside the switching lens group and a conjugate of the entrance pupil of the OCT imaging module located between the ocular lens and the OCT imaging module, the new pupil conjugate is on or near the focal plane of the ocular lens, and the distance from the ocular lens to the eye under test in the anterior segment imaging mode is the same or nearly the same as in the retina imaging mode; and
    in the anterior segment imaging mode, the light incident on the eye is parallel or nearly parallel thus achieving telecentric or nearly telecentric imaging of the anterior segment.

2. The ophthalmic imaging system according to claim 1, further comprising a first dichroic mirror, wherein the OCT imaging module is positioned on one side of the first dichroic mirror, the ocular lens is positioned on the reflective light path or the transmissive path of the first dichroic mirror, and the first intermediate image plane is located between the ocular lens and the first dichroic mirror.

3. The ophthalmic imaging system according to claim 1, wherein the optical path ratio of the retina imaging mode and the anterior segment imaging mode of the OCT imaging module satisfies the following formula:

$$0.9 \le \frac{OPL_{retina}}{OPL_{cornea}} \le 1.1,$$

wherein $OPL_{retina}$ represents the optical path length of the retina imaging mode measured from the entrance pupil of the OCT imaging module to the retina of a standard eye, and $OPL_{cornea}$ represents the optical path length of the anterior segment imaging mode measured from the entrance pupil of the OCT imaging module to the iris of the standard eye.

4. The ophthalmic imaging system according to claim 2, further comprising a second dichroic mirror and a scanning laser ophthalmoscope (SLO) module, wherein the second dichroic mirror is positioned on the transmissive path or the reflective path of the first dichroic mirror, a first relay device is positioned on the light path between the second dichroic mirror and the first dichroic mirror, and the SLO module is positioned on the reflective path or the transmissive path of the second dichroic mirror.

5. The ophthalmic imaging system according to claim 4, further comprising a third dichroic mirror, a fixation target module and an pupil camera module, wherein the third dichroic mirror is positioned on the transmissive light path or the reflective path of the second dichroic mirror, a second relay device is positioned between the third dichroic mirror and the second dichroic mirror, the fixation target module is positioned on the transmissive path or a reflective path of the third dichroic mirror, and the pupil camera module is positioned on the reflective light path or the transmissive light path of the third dichroic mirror.

6. The ophthalmic imaging system according to claim 2, further comprising an OCT galvanometer, wherein the OCT galvanometer is positioned at the end, away from the first dichroic mirror, of the OCT imaging module.

7. The ophthalmic imaging system according to claim 1, wherein the OCT imaging module comprises a first lens group, the first lens group comprises a first lens and a second lens, the first lens is close to the ocular lens, the second lens is away from the ocular lens, and the OCT imaging module further comprises a third lens positioned on the side, away from the ocular lens, of the first lens group.

8. The ophthalmic imaging system according to claim 7, wherein the switching lens group is positioned between the second lens and the third lens.

9. The ophthalmic imaging system according to claim 7, wherein the switching lens group comprises a second lens group and a third lens group, positioned on both sides of the second intermediate image plane respectively.

10. The ophthalmic imaging system according to claim 9, wherein the second lens group comprises a fourth lens, the third lens group comprises a fifth lens and a sixth lens, and the fifth lens and the sixth lens are sequentially away from the second intermediate image plane.

11. The ophthalmic imaging system according to claim 9, wherein the second lens group comprises a fourth lens and a fifth lens, the fifth lens and the fourth lens are sequentially away from the second intermediate image plane, the third lens group comprises a sixth lens, a seventh lens and an eighth lens, and the sixth lens, the seventh lens and the eighth lens are sequentially away from the second intermediate image plane.

12. The ophthalmic imaging system according to claim 1, wherein the ophthalmic imaging system further comprises a lens group switching device, and the lens group switching device switches the switching lens group to between the retina imaging mode and the anterior segment imaging mode.

13. The ophthalmic imaging system according to claim 12, wherein the lens group switching device comprises:
    a base plate, wherein the switching lens group is mounted in the base plate through a positioning block;
    a driving platform vertically fixed on the base plate; and
    a driving motor, wherein a ball screw connected with a rotating shaft of the driving motor is fixed on a horizontal part of the driving platform, a guide rail is fixed on a vertical part of the driving platform, and the vertical part of the driving platform is equipped with two photoelectric sensors in the longitudinal direction,
    wherein the switching lens group assembly comprises a lens group and a prepressing plate which is elastically connected with the lens group, wherein a feed screw nut is connected with the ball screw, a slider capable of moving up and down along the guide rail is fixed on the prepressing plate, and a mechanical triggering part to trigger the two photoelectric sensors is also connected with the prepressing plate.

14. The ophthalmic imaging system according to claim 13, wherein the ball screw is fixed in the base plate after passing through the feed screw nut and the prepressing plate.

15. The ophthalmic imaging system according to claim 13, wherein the bottom of the switching lens group assembly is equipped with an annular positioning area, a set of magnets are equidistantly mounted on the annular positioning area, a V-shaped groove is provided between each pair of adjacent magnets, and the V-shaped grooves are also equidistantly arranged in the annular positioning area, wherein the base plate is also equipped with an annular positioning part, a set of magnets are equidistantly mounted on the annular positioning part, a metal or ceramic ball is provided between each pair of adjacent magnets, and the metal or ceramic balls are equidistantly arranged in the annular positioning part, wherein the magnets at the bottom of the lens group and the magnets on the base plate are arranged correspondingly, and the metal or ceramic balls are in kinetic contact with the V-shaped grooves when the switching lens group assembly is switched onto the base plate.

16. The ophthalmic imaging system according to claim 13, wherein the base plate of the switching lens group assembly is equipped with through holes, the prepressing plate contains equal number of matching threaded holes corresponding to the through holes, the lens group and the prepressing plate are connected through connecting screws, which are sheathed in springs, wherein the connecting screws sequentially pass through the springs and the through holes and are connected with the threaded holes by threads.

* * * * *